(12) United States Patent
Johannessen et al.

(10) Patent No.: US 12,121,621 B2
(45) Date of Patent: Oct. 22, 2024

(54) SANITIZATION SYSTEMS AND METHODS (71) Applicant: B/E AEROSPACE, INC., Winston Salem, NC (US)

(72) Inventors: Eric Johannessen, Holbrook, NY (US); Matthew Pearson, Hartford, CT (US); Joseph Mantese, Ellington, CT (US)

(73) Assignee: B/E AEROSPACE, INC., Winston Salem, NC (US)

( * ) Notice: Subject to any disclaimer, the term of this patent is extended or adjusted under 35 U.S.C. 154(b) by 496 days.

(21) Appl. No.: 17/372,280

(22) Filed: Jul. 9, 2021

(65) Prior Publication Data
US 2023/0009835 A1 Jan. 12, 2023

(51) Int. Cl.
*A61L 2/10* (2006.01)
*A61L 2/08* (2006.01)
*A61L 2/26* (2006.01)

(52) U.S. Cl.
CPC ............... *A61L 2/10* (2013.01); *A61L 2/084* (2013.01); *A61L 2/26* (2013.01); *A61L 2202/11* (2013.01); *A61L 2202/16* (2013.01); *A61L 2202/25* (2013.01)

(58) Field of Classification Search
None
See application file for complete search history.

(56) References Cited

U.S. PATENT DOCUMENTS

2004/0120844 A1 6/2004 Tribelsky et al.
2004/0219056 A1 11/2004 Tribelsky et al.
2017/0290932 A1* 10/2017 Mori ................... A61N 5/0613
2019/0030195 A1* 1/2019 Hatti ......................... A61L 2/24
2020/0073199 A1* 3/2020 Lin ....................... A61L 2/0047
2021/0113724 A1* 4/2021 Ufkes ........................ A61L 9/20

OTHER PUBLICATIONS

Buonanno, M., Welch, D., Shuryak, I. et al., "Far-UVC light (222 nm) efficiently and safely inactivates airborne human coronaviruses", Scientific Reports 10 10285 (2020), pp. 1-8, https://doi.org/10.1038/s41598-020-67211-2.
Ruhnke et al, "Compact Deep UV System at 222.5 nm Base on Frequency Doubling of GaN Laser Diode Emission", IEEE Photonics Technology Letters, vol. 30., No. 3, dated Feb. 1, 2018, pp. 289-292, XP055956491, ISSN: 1041-11355, DOI: 10.1109/LTP.2017.2787463, Retrieved from the Internet: url: https://ieee.org/stampPDF/getPDF.jsp?tp=&arnumber=8245783&ref=aHR0cHM6Ly9pZWVVtZW50LzgyNDU3ODM=>.
European Patent Office, European Search Report dated Apr. 3, 2023 in Application No. 22183430.2.

* cited by examiner

*Primary Examiner* — Eliza W Osenbaugh-Stewart
(74) *Attorney, Agent, or Firm* — SNELL & WILMER L.L.P.

(57) ABSTRACT

A sanitization apparatus may comprise a light source configured to emit a light having a first wavelength between 414 and 474 nm; a nonlinear crystal disposed proximal to the light source, the nonlinear crystal configured to receive the light having the first wavelength and output a first portion of the light having the first wavelength and a second portion of the light having a second wavelength, the second wavelength being half the first wavelength; and a prism configured to receive the first portion of the light and the second portion of the light, the prism configured to direct the second portion of the light toward a surface to be sanitized.

17 Claims, 7 Drawing Sheets

SANITIZATION SYSTEMS AND METHODS

FIELD

The present disclosure relates generally to sanitization systems and methods and, more particularly, to sanitization systems and method using frequency doubling to generate FAR-UVC for aircrafts.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization apparatus is disclosed herein. The sanitization apparatus may comprise a light source configured to emit a light having a first wavelength between 414 and 474 nm; a nonlinear crystal disposed proximal to the light source, the nonlinear crystal configured to receive the light having the first wavelength and output a first portion of the light having the first wavelength and a second portion of the light having a second wavelength, the second wavelength being half the first wavelength; and a prism configured to receive the first portion of the light and the second portion of the light, the prism configured to direct the second portion of the light toward a surface to be sanitized.

In various embodiments, the second wavelength is between 207 and 237 nm. The nonlinear crystal may be configured to for second harmonic generation (SHG). The first portion of the light and the second portion of the light may be collimated. The first portion of the light may provide a visual indication that the surface is being sanitized. The light source may be one of a laser pump or a light emitting diode (LED).

A sanitization system for an aircraft is disclosed herein. The sanitization system may comprise: a controller; and a sanitization apparatus in operable communication with the controller, the sanitization apparatus comprising a light source configured to emit a light having a first wavelength between 414 and 474 nm and a nonlinear crystal configured to convert a portion of the light from the light source to a second wavelength between 207 and 237 nm, the controller configured to command the sanitization apparatus to scan a predetermined area.

In various embodiments, the sanitization apparatus is configured to direct a beam of the portion of the light having the second wavelength toward the predetermined area. The sanitization apparatus may be further configured to direct a second beam that is collimated with the beam toward the predetermined area. The second beam may include the first wavelength. The second beam may provide a visual indication that the predetermined area is being sanitized. The sanitization system may further comprise a plurality of the sanitization apparatus. The sanitization apparatus may be configured to scan the predetermined area with the portion of the light having the second wavelength in response to receiving the command to scan the predetermined area. The sanitization system may further comprise a passenger service unit including the sanitization apparatus.

A method of sanitizing a surface is disclosed herein. The method may comprise: generating a light having a first wavelength between 414 and 474 nm; converting the light into a first portion of the light having the first wavelength and a second portion of the light having a second wavelength, the second wavelength being half the first wavelength; and directing the second portion of the light toward the surface to be sanitized.

In various embodiments, generating the light having the first wavelength is through one of a laser pump or a light emitting diode (LED). In various embodiments, converting the light is through a nonlinear crystal. In various embodiments, directing the second portion of the light toward the surface is through a prism. The method may further comprise directing the first portion of the light in a first direction that is collimated with a second direction of the second portion of the light. The method may further comprise scanning a predetermined area of the surface with the second portion of the light.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In various embodiments, Far-UV (222 nm wavelength light) has promise to work in occupied spaces but may utilize significant power to disinfect an entirety of a cabin. Additionally, Far-UV (222 nm wavelength light) may have limitations as to total dosage a human may receive. In various embodiments, integrating Far-UV (222 nm wavelength light) via excimer lamps would be relatively expensive and utilize heavy high power intensity light sources, such as excimer lamps. Excimer lamps utilize a high voltage supply and have a large gas discharge. In various embodiments, the systems and methods disclosed herein are configured to generate a first light with a first wavelength, convert a portion of the first light to a second light with a second wavelength, the second wavelength being half the first wavelength, and/or maintain a portion of the first light as an indicator. In various embodiments, the first wavelength is between 414 nm and 474 nm, or between 429 nm and 459 nm, or approximately 444 nm.

In various embodiments, the sanitization system disclosed herein, may enable an output light of Far-UV (222 nm wavelength light) to actively disinfect surfaces during flight in a safe manner while limiting power restrictions via low voltage light source and a sanitization apparatus configured for frequency doubling.

Figure 1:
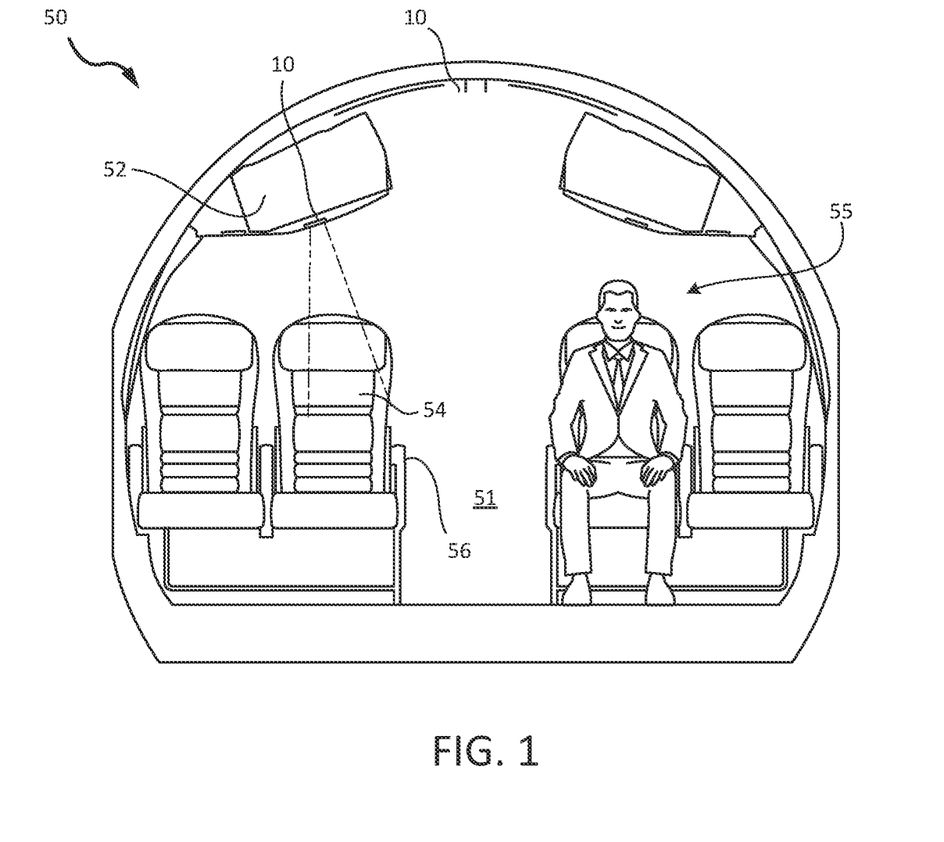
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
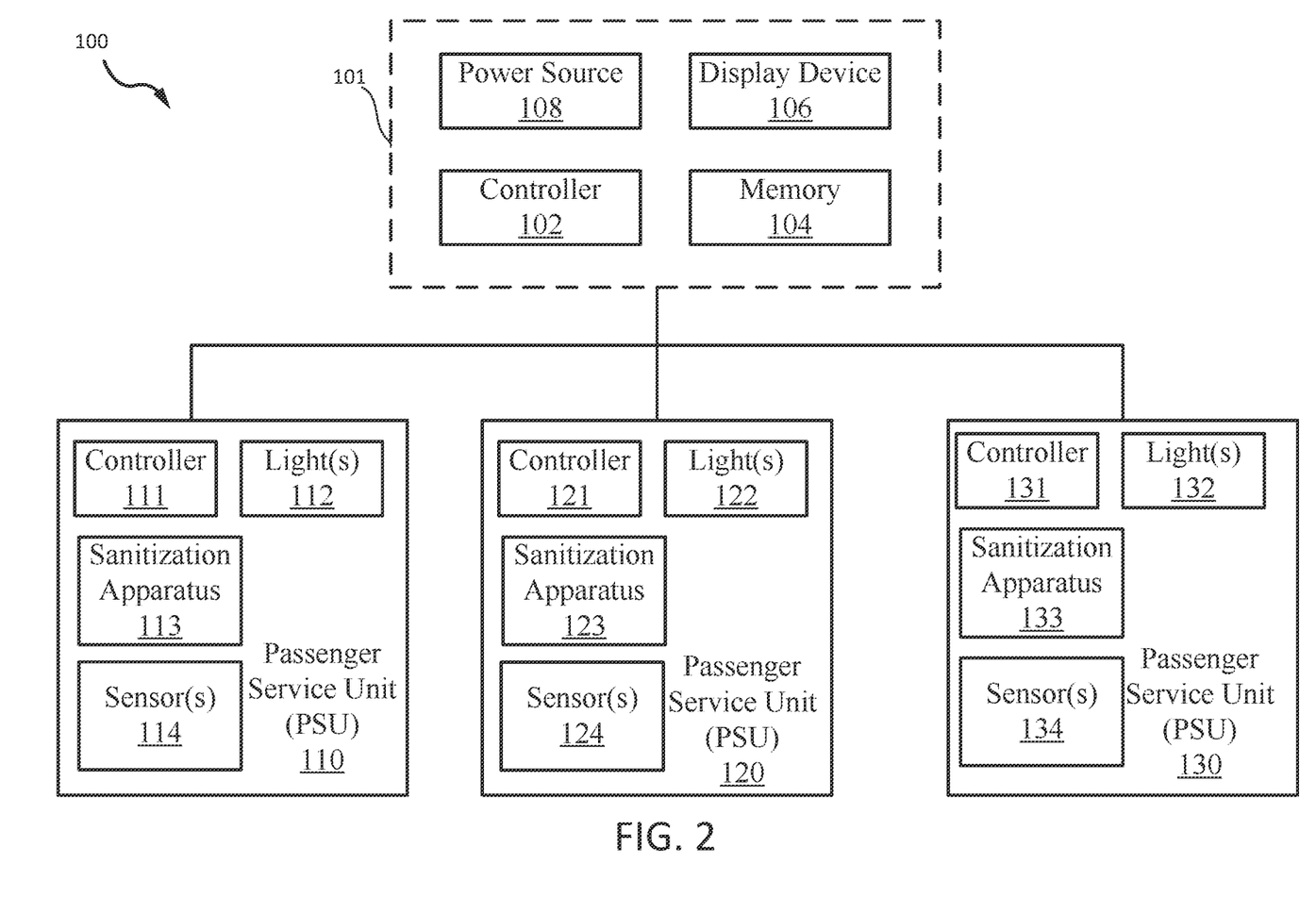
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104, any appropriate data storage architecture may be utilized by the memory 104, or both.

The database 104 may be integral to the control system 101 or may be located remote from the control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may can include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se.

Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, cleaning a specific row in response to a trigger (i.e., a sneeze or the like), etc.

In various embodiments, the main control system 101 from FIG. 2 further comprises a power source 108 and a display device 106. The power source 108 may comprise any power source known in the art, such as a battery, a solar source, an alternating current (AC) source, a rechargeable source, or the like. In various embodiments, the display device 106 may be configured to provide inputs into the control system 101 and alternate between various modes (e.g., alternating from an in-flight mode to a post-flight mode or the like). In various embodiments, the sanitization system 100 may alternate modes automatically in response to detecting a change in mode is desired, as described further herein.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102). For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory known in the art. The memory may store instructions usable by the logic device to perform operations. Any appropriate computer-readable type/configuration may be utilized as the memory, any appropriate data storage architecture may be utilized by the memory, or both.

In various embodiments, each PSU (e.g., PSUs 110, 120, 130) may comprise light(s) (e.g., light(s) 112, 122, 132), a sanitization apparatus (e.g., sanitization apparatus 113, 123, 133), and/or sensor(s) (e.g., sensors 114, 124, 134), and a local energy storage device (e.g., energy storage 115, 125, 135). As described further herein, the controller 102 may command the various local controllers (e.g., controllers 111, 121, 131) to instruct the devices therein. In various embodiments, the local energy storage device (e.g., energy storage 115, 125, 135) may comprise any electrical storage device, such as a capacitor, a supercapacitor, a superconducting magnetic storage, or the like.

In various embodiments, the power source 108 is sized and configured to power all of the lights (e.g., light(s) 112, 122, 132, etc.) of all of the PSUs (e.g., PSUs 110, 120, 130, etc.) of a sanitization system 100. Since the sanitization apparatuses (113, 123, 133) utilize a light source having a wavelength between 414 nm and 474 nm, significantly less power may be utilized during a sanitization process as disclosed further herein. In this regard, the power source 108 may be kept similar to a typical power source 108 for an aircraft cabin control system, in accordance with various embodiments.

In various embodiments there may be a single sensor or a plurality of sensors for each PSU. For example, sensor(s) (e.g., sensor(s) 114, 124, 134) may each include a microphone array, an occupancy sensor, a manual trigger, or a combination thereof. In this regard, the sanitization system 100 may be configured to detect occupancy and/or configured to detect an event where cleaning may be desired, such as a detecting a sneeze, a cough, or the like.

In various embodiments, each sanitization apparatus (e.g., sanitization apparatus 113, 123, 133) may be connected via digital communications, discrete communications, or wireless communications to a respective local controller (e.g., controllers 111, 121, 131). In various embodiments, a respective local controller may be configured to monitor a health of a respective sanitizer, as well as a life of a respective sanitization apparatus. For example, controller 111 may be configured to receive light source life data from the sanitization apparatus 113, each PSU (e.g., PSUs 110, 120, 130) may be configured to track a total dosage of FAR-UV supplied to a given area. For example, the controller 111 of PSU 110 may receive a duration that sanitization apparatus 113 has been in operation and limit operation when a threshold dosage is being approached.

Figure 3A:
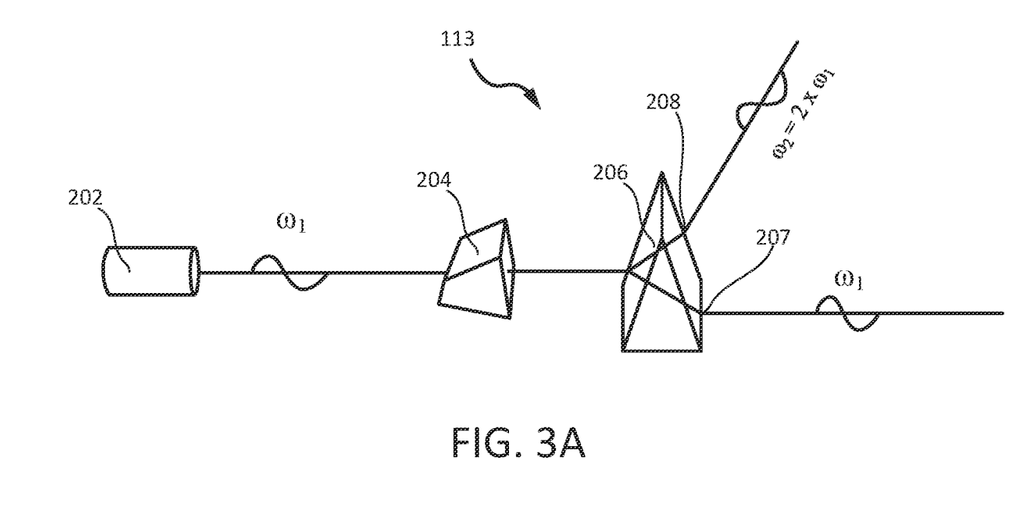
FIG. 3A illustrates a schematic view of a sanitization apparatus, in accordance with various embodiments.

Referring now to FIG. 3A, a schematic view of the sanitization apparatus 113 from FIG. 2, in accordance with various embodiments. In various embodiments, the sanitization apparatus 113 comprises a light source 202. In various embodiments, the light source 202 may comprise a light emitting diode (LED), a Nd:YAG/LBO laser, a InGaN laser diode, an InGaN laser pump source or the like. In various embodiments, any light source capable of generating a light with a first wavelength between 414 nm and 474 nm is within the scope of this disclosure. In various embodiments, the light source may weigh significantly less than a light source capable of generating a UVC wavelength (e.g., between 200 nm and 280 nm). In various embodiments, the light source 202 is in operable communication with a controller (e.g., a local controller 111 from FIG. 1 and/or a main controller 102). In this regard, in response to receiving a signal from a controller, the light source 202 may be activated and generate a wavelength between 414 nm and 474 nm, or between 429 and 459 nm, or approximately 444 nm.

In various embodiments, the sanitization apparatus 113 further comprises a nonlinear crystal 204. The nonlinear crystal 204 is configured to double a frequency of a portion of an incoming light, in accordance with various embodiments. In various embodiments, the non-linear crystal 204 is configured for second harmonic generation (SHG). In various embodiments, it may be desirable to use a crystal material which can be critically phase-matched at room temperature, because noncritical phase matching often involves the operation of the crystal in a temperature-stabilized crystal oven.

In various embodiments, the nonlinear crystal 204 may be any nonlinear crystal configured for frequency doubling, such as lithium niobate, lithium tantalate, potassium niobate, potassium titanyl phosphate, potassium dihydrogen phosphate, potassium dideuterium phosphate, lithium triborate, cesium lithium borate, β-barium borate, bismuth triborate, cesium borate, yttrium calcium oxyborate, strontium beryllium borate, zinc germanium diphosphide, silver gallium sulfide and elenide, gallium selenide, cadmium selenide, or the like. The present disclosure is not limited in this regard.

Figure 3B:
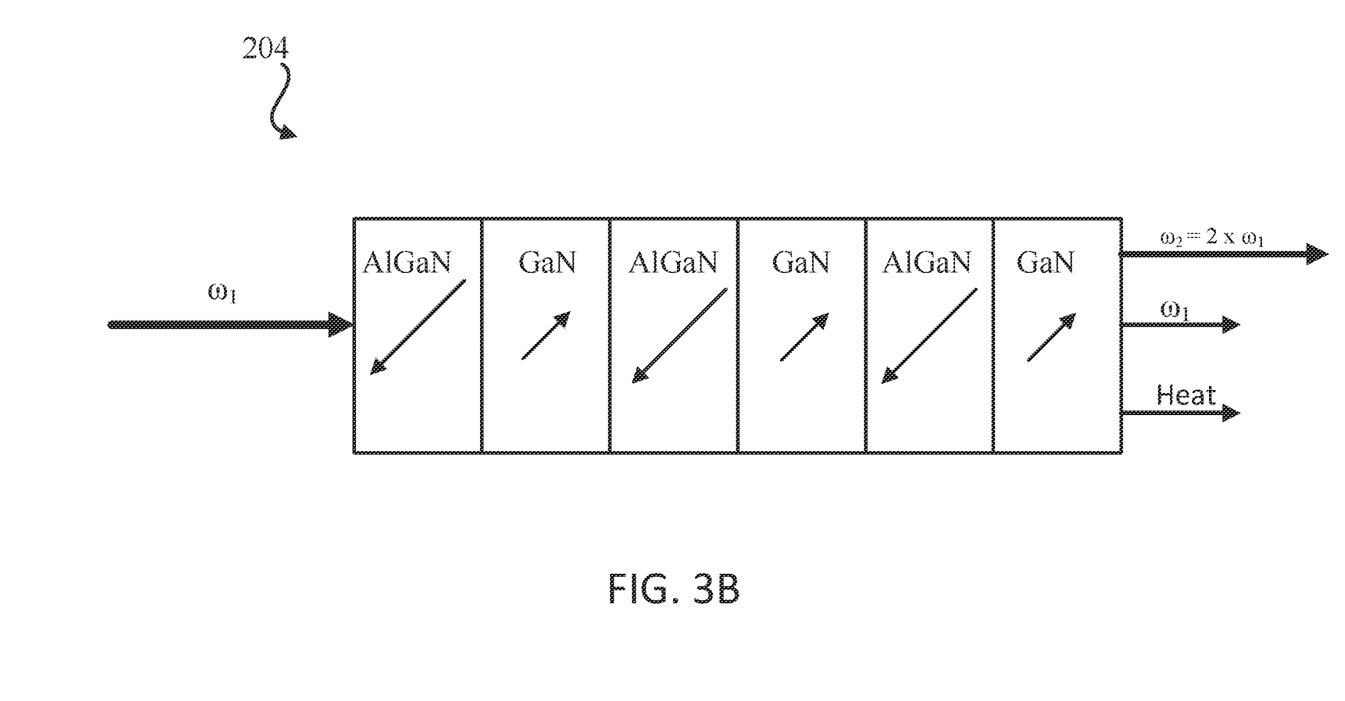
FIG. 3B illustrates a schematic view of a nonlinear crystal, in accordance with various embodiments.

With brief reference now to FIG. 3B, a nonlinear crystal 204 in accordance with various embodiments, is illustrated. The nonlinear crystal 204 may comprise alternating layers of a first semiconductor and a second semiconductor. For example, the first semiconductor may comprise Alumina Gallium Nitride and the second semiconductor may comprise Gallium Nitride. The nonlinear crystal 204 is configured for second harmonic generation. In this regard, two photons of the same frequency interact with the nonlinear crystal 204, are combined, and generate a new photon with twice the energy of the initial photons individually. In various embodiments, as illustrated light having a first wavelength enters the nonlinear crystal 204 where nonlinear phase-matching stores energy within the nonlinear crystal and outputs a second harmonic wave (e.g., $\omega_2 = 2 \times \omega_1$), a residual wave having the same wavelength as the input, and heat. In various embodiments, the second harmonic wave may have less energy relative to the input wave (e.g., between 3% and 10%). In this regard, the light converter 230 may have similar or better efficiency compared to UVC light sources, such as excimer lamps, which have approximately 3% efficiency. Thus, the systems and methods disclosed herein may result in a significantly lighter, portable, and/or less expensive UVC sanitization device, in accordance with various embodiments.

In various embodiments, the nonlinear crystal 204 is configured to receive a light having a first wavelength and output a first portion of the light with the first wavelength, a second portion of the light with a second wavelength, the second wavelength half the first wavelength, and heat.

In various embodiments, the output from the nonlinear crystal 204 is received by a prism 206 configured to direct the light received from the nonlinear crystal. For example, the first portion of the light with the first wavelength may directed through first output 207 of the prism 206 and the second portion of the light with the second wavelength may be directed through a second output 208. In various embodiments, the first output and the second output may be collimated (i.e., parallel or the like). In this regard, the first wavelength may indicate to a person that the area is being sanitized as the first wavelength would have greater visibility relative to the second wavelength, in accordance with various embodiments. Although illustrated as being separated, the first wavelength and the second wavelength may be coaxial in accordance with various embodiments. In this regard the first wavelength may indicate more clearly a location being sanitized, in accordance with various embodiments. Additionally, in various embodiments, the residual light of the first wavelength through output 207 may be mixed with an additional light source (e.g., light(s) 112 from FIG. 2) to create white light, such as for use as a reading light or the like. Although described with respect to sanitization apparatus 113, any sanitization apparatus disclosed herein (e.g., sanitization apparatuses 123, 133) may be in accordance with sanitization apparatus 113 from FIG. 3, in accordance with various embodiments.

Figure 4:
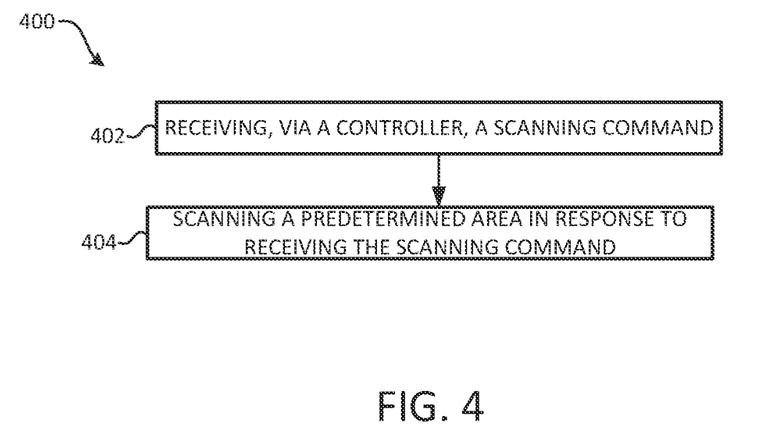
FIG. 4 is a process performed by a control system for a sanitization system, in accordance with various embodiments.

Referring now to FIG. 4, a method of sanitization a portion of an aircraft is illustrated, in accordance with various embodiments. The method may comprise receiving, via a controller, a scanning command (step 402). The scanning command may include a predefined area. In various embodiments, since the output from the prism of 206 of the sanitization apparatus 113 is a beam, it can be directed in a manner similar to a barcode scanner or the like. In contrast, excimer lamps, and other far-UV light sources cannot generate a beam or light that can be directed. Thus, the systems and methods disclosed herein may facilitate scanning areas and avoiding people when sanitizing a particular area. In this regard, sensor(s) 114, 124, 134 from FIG. 2 may include infrared sensors, LiDAR sensors, or the like. The sensors may be configured to detect and identify people, and the controller (e.g., main controller 102 or local controllers 111, 121, 131) may be configured to command the sanitization apparatus to direct the output beam(s) away from people, in accordance with various embodiments.

The method 400 may further comprise scanning a predetermined area in response to receiving the scanning command (step 404). In various embodiments, the predetermined area may be an area that commonly comes into contact with passengers, such as tray tables, arm rests, or the like. In various embodiments, scanning the predetermined area may be an active scanning where portions of the area are avoided in response to detecting a person as described previously herein.

Figure 5:
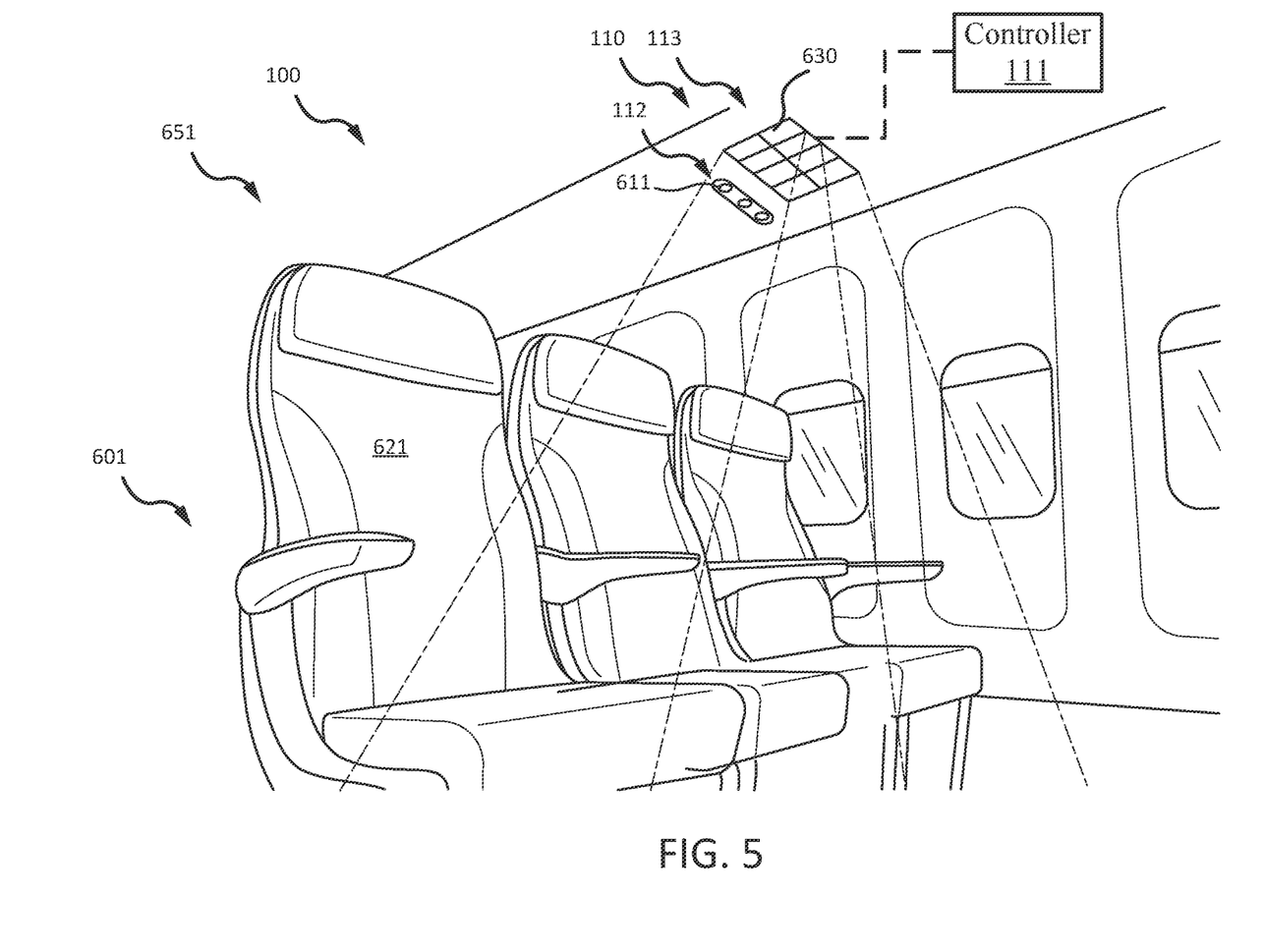
FIG. 5 is a perspective view of a portion of a sanitization system 100, in accordance with various embodiments.

Referring now to FIG. 5, a perspective view of a portion of the sanitization system 100 from FIG. 2 is illustrated, in accordance with various embodiments. The sanitization system 100 includes the light(s) 112 and the sanitization apparatus 113. In various embodiments, each light light(s) 112 may correspond to a seat in a respective row. For example, a first light 611 may be configured to align towards a first seat 621 in a row 601 of in the aircraft cabin 651. In this regard, each light in the light(s) 112 in a PSU 110 may be configured to emit light towards a seat in a row of the respective PSU 110.

In various embodiments, the sanitization apparatus 113 in a PSU 110 includes the light source 602, the nonlinear crystal 604, and the prism 606 from FIG. 2. Although illustrated as including a plurality of the sanitization apparatus 113, any number of sanitization apparatuses 113 for a respective PSU 110 is within the scope of this disclosure. In various embodiments, the local controller 111 (or main controller 102) from FIG. 2 may adjust a beam direction of a respective sanitization apparatus 630 in the plurality of the sanitization apparatus 113 during a sanitization process (e.g., method 400). In various embodiments, the sanitization system 100 may be configured to direct the light away from a passenger's head (e.g., towards the tray tables, or the like).

Figure 6:
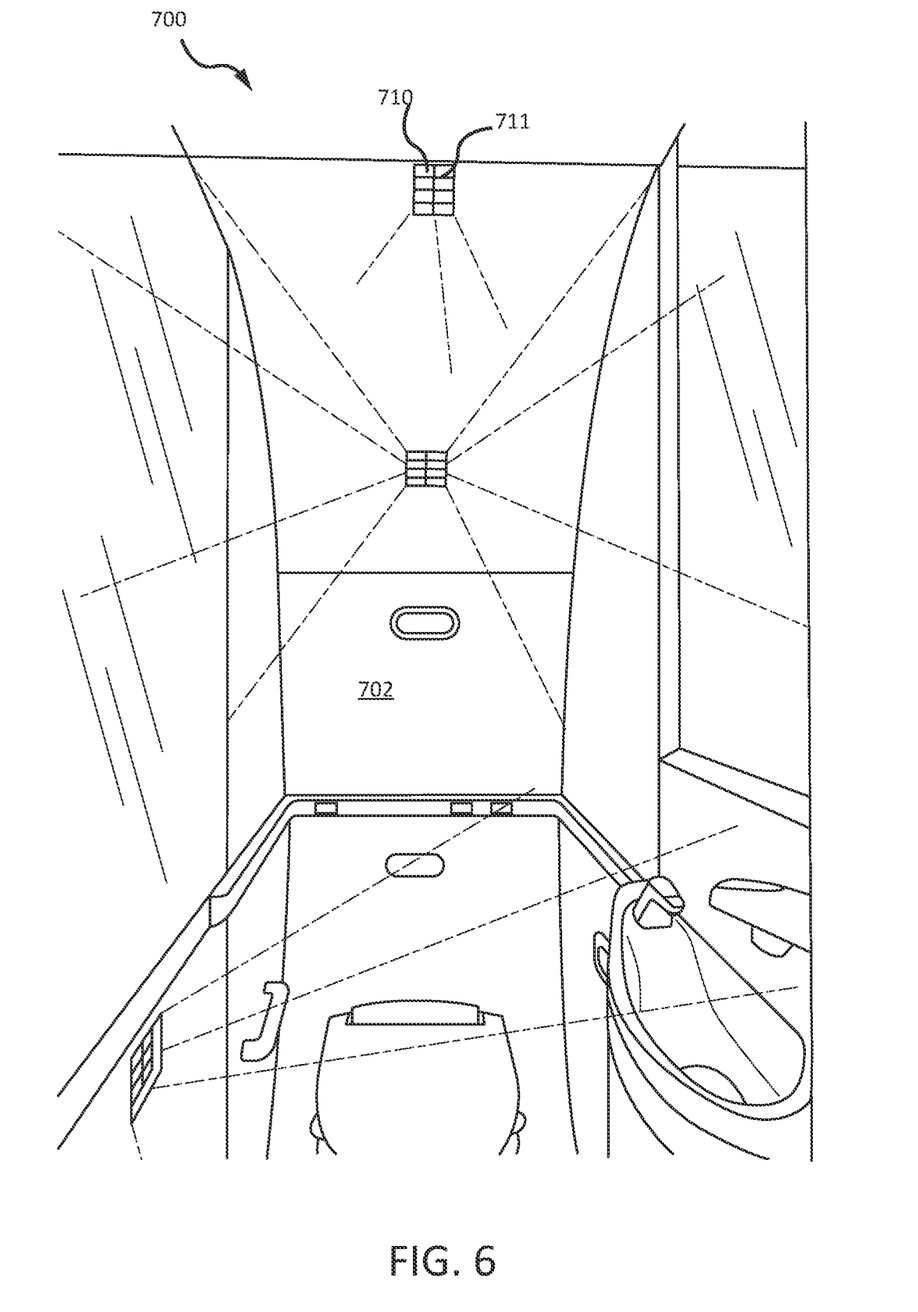
FIG. 6 is a perspective view of a lavatory in an aircraft, in accordance with various embodiments.

Referring now to FIG. 6, a perspective view of a sanitization system 700 is illustrated, in accordance with various embodiments. In various embodiments, the sanitization system 700 may be disposed in a lavatory 702 of an aircraft cabin (e.g., aircraft cabin 51 from FIG. 1). In this regard, the sanitization system 700 may be configured in a manner similar to sanitization system 100. For example, the sanitization system may include sensor(s) configured to detect whether the bathroom is occupied (e.g., sensor(s) 114 from FIG. 2), a sanitization apparatus 710 (e.g., sanitization apparatus 113), and a controller (e.g., controller 111 from FIG. 1). In various embodiments, the sanitization system 700 may be in communication with main controller 102 from the sanitization system 100 from FIG. 2. In this regard, the lavatory 702 may be configured to be sanitized during in-flight cycle, post-flight cycle, or the like. In various embodiments, the lavatory 702 may be configured to be sanitized after use (e.g., in response to detecting a user entering and detecting a user leaving).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization system for an aircraft, the sanitization system, comprising:
   one or more controllers;
   a plurality of passenger service units (PSUs), each of the plurality of PSUs comprising a sanitization apparatus in operable communication with the one or more controllers, the sanitization apparatus comprising:
   a light source configured to emit a light having a first wavelength between 414 and 474 nm;
   a nonlinear crystal that is disposed proximal to the light source, the nonlinear crystal configured to receive the light having the first wavelength and output a first portion of the light having the first wavelength and a second portion of the light having a second wavelength, the second wavelength being half the first wavelength, the nonlinear crystal comprising alternating layers of a first semiconductor and a second semiconductor, the first semiconductor comprising alumina gallium nitride, and the second semiconductor comprising gallium nitride; and
   a prism configured to receive the first portion of the light and the second portion of the light, the prism configured to direct the second portion of the light toward a surface to be sanitized, wherein the one or more controllers is configured to:
   command the sanitization apparatus to scan a predetermined area, and
   limit operation of the sanitization apparatus in one of the plurality of PSUs in response to a threshold dosage being one of met, approached or exceeded.

2. The sanitization apparatus of claim 1, wherein the second wavelength is between 207 and 237 nm.

3. The sanitization apparatus of claim 1, wherein the nonlinear crystal is configured to for second harmonic generation (SHG).

4. The sanitization apparatus of claim 1, wherein the first portion of the light and the second portion of the light are collimated.

5. The sanitization apparatus of claim 4, wherein the first portion of the light provides a visual indication that the surface is being sanitized.

6. The sanitization apparatus of claim 1, wherein the light source is a light emitting diode (LED).

7. The sanitization system of claim 1, wherein the sanitization apparatus is configured to direct a first beam of the second portion of the light having the second wavelength toward the predetermined area.

8. The sanitization system of claim 7, wherein the sanitization apparatus is further configured to direct a second beam that is collimated with the beam toward the predetermined area.

9. The sanitization system of claim 8, wherein the second beam includes the first wavelength.

10. The sanitization system of claim 8, wherein the second beam provides a visual indication that the predetermined area is being sanitized.

11. The sanitization system of claim 1, wherein the sanitization apparatus is configured to scan the predetermined area with the second portion of the light having the second wavelength in response to receiving the command to scan the predetermined area.

12. The sanitization system of claim 1, wherein each of the plurality of PSUs further comprise a sensor, and wherein the one or more controllers is further configured to command the sanitization apparatus to direct an output beam of the sanitization apparatus away from people based on the sensor detecting the people.

13. The sanitization system of claim 1, wherein each of the plurality of PSUs further comprises a second light source, and wherein the second light source is configured to emit a second light and mix the second light with the first portion of the light having the first wavelength to generate a reading light.

14. A method of sanitizing a surface, comprising:
generating, via a sanitization apparatus, a light having a first wavelength between 414 and 474 nm;
converting, via a nonlinear crystal of the sanitization apparatus, the light into a first portion of the light having the first wavelength and a second portion of the light having a second wavelength, the second wavelength being half the first wavelength, the nonlinear crystal comprising alternating layers of a first semiconductor and a second semiconductor, the first semiconductor comprising alumina gallium nitride, and the second semiconductor comprising gallium nitride;
directing, via the sanitization apparatus, the second portion of the light toward the surface to be sanitized;
scanning, via the sanitization apparatus, a predetermined area of the surface with the second portion of the light; and
limiting operation of the sanitization apparatus in response to a threshold dosage being one of met, approached or exceeded.

15. The method of claim 14, wherein generating the light having the first wavelength is through one of a laser pump or a light emitting diode (LED).

16. The method of claim 14, wherein directing the second portion of the light toward the surface is through a prism.

17. The method of claim 14, further comprising directing the first portion of the light in a first direction that is collimated with a second direction of the second portion of the light.

* * * * *